(12) United States Patent
Tchakalova et al.

(10) Patent No.: US 11,331,639 B2
(45) Date of Patent: May 17, 2022

(54) HYDROGEL BEADS

(71) Applicant: Firmenich SA, Satigny (CH)

(72) Inventors: Vera Tchakalova, Satigny (CH); Laura Mesmin, Satigny (CH); Nathalie Thiebaut, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/754,367

(22) PCT Filed: Oct. 18, 2018

(86) PCT No.: PCT/EP2018/078581
§ 371 (c)(1),
(2) Date: Apr. 7, 2020

(87) PCT Pub. No.: WO2019/077052
PCT Pub. Date: Apr. 25, 2019

(65) Prior Publication Data
US 2020/0238244 A1 Jul. 30, 2020

(30) Foreign Application Priority Data
Oct. 19, 2017 (EP) .................................... 17197397

(51) Int. Cl.
| | |
|---|---|
| *B01J 13/06* | (2006.01) |
| *C11B 9/00* | (2006.01) |
| *A61K 8/02* | (2006.01) |
| *A61K 8/04* | (2006.01) |
| *A61K 8/11* | (2006.01) |
| *A61K 8/73* | (2006.01) |
| *A61K 8/37* | (2006.01) |
| *A61Q 13/00* | (2006.01) |
| *A61Q 19/10* | (2006.01) |
| *A61Q 19/00* | (2006.01) |
| *A61Q 11/00* | (2006.01) |
| *A61Q 5/02* | (2006.01) |
| *A23L 27/00* | (2016.01) |

(52) U.S. Cl.
CPC .............. *B01J 13/06* (2013.01); *A23L 27/74* (2016.08); *A61K 8/0295* (2013.01); *A61K 8/042* (2013.01); *A61K 8/11* (2013.01); *A61K 8/375* (2013.01); *A61K 8/733* (2013.01); *A61Q 5/02* (2013.01); *A61Q 11/00* (2013.01); *A61Q 13/00* (2013.01); *A61Q 19/007* (2013.01); *A61Q 19/10* (2013.01); *C11B 9/00* (2013.01); *A23V 2002/00* (2013.01)

(58) Field of Classification Search
CPC ...... A61K 8/0295; A61K 8/375; A61K 8/342; A61K 8/042; A61K 8/11; A61K 8/733; A23L 27/74; A61Q 19/10; A61Q 19/007; A61Q 19/00; C11B 9/00; B01J 13/06
See application file for complete search history.

(56) References Cited

U.S. PATENT DOCUMENTS

| | | |
|---|---|---|
| 6,319,507 B1 | 11/2001 | Delrieu et al. |
| 2002/0034525 A1* | 3/2002 | Sakai ............... A61P 17/00 424/401 |
| 2006/0292280 A1 | 12/2006 | Soper et al. |
| 2008/0044481 A1 | 2/2008 | Harel |
| 2014/0274865 A1* | 9/2014 | Restrepo ............ A61K 8/042 510/403 |
| 2015/0306020 A1 | 10/2015 | Kershner et al. |
| 2018/0078468 A1 | 3/2018 | Huda et al. |

FOREIGN PATENT DOCUMENTS

WO 2012/089819 A1 7/2012

OTHER PUBLICATIONS

International Search Report and Written Opinion for International Application No. PCT/EP2018/078581 dated Dec. 20, 2018. 15 pages.

* cited by examiner

*Primary Examiner* — Anna R Falkowitz

(57) ABSTRACT

The present invention relates to hydrogel beads having liquid crystalline structured phase. Process for preparing crystalline hydrogel beads is also an object of the invention. Perfuming compositions and consumer products comprising or consisting of said crystalline beads, in particular perfumed consumer products in the form of a personal care products or flavoured products, are also part of the invention.

11 Claims, 4 Drawing Sheets

HYDROGEL BEADS

TECHNICAL FIELD

The present invention relates to hydrogel beads. Process for preparing hydrogel beads is also an object of the invention. Perfuming compositions and consumer products comprising or consisting of said hydrogel beads, in particular perfumed consumer products in the form of a personal care products or flavoured products, are also part of the invention.

BACKGROUND OF THE INVENTION

Fragrances play an important role in the perception of consumer product performance and thus they often determine the consumer's choice for a given product. In addition, the increasing consumer demand for fragrance experience is driving the development of new delivery systems.

Biopolymer hydrogels are used in many different domains such as cosmetics, pharmaceuticals and foods. Due to their nontoxicity, biodegradability and hypo-allergenicity they are preferred ingredients in a lot of applications. In many industries, hydrogel capsules have been adapted as delivery systems for holding and/or delivering various molecules of interest that can be deposited within the core spaces of hydrogel. Typically, the resulting capsule has a structure comprising a hydrophobic core enclosed within a hydrophilic hydrogel matrix that can support substantial amount of water (e.g. at least 70%).

A key requirement from the industry regarding these delivery systems is to survive suspension in challenging bases without physically dissociating or degrading. For instance, fragranced personal and household cleansers containing high levels of aggressive surfactant detergents are very challenging for the stability of such system.

US2006/0292280 discloses alginate particles with heterogeneous matrix composed of a polymer gel continuous phase and an oily discontinuous phase including optionally actives.

WO 2012/089819 describes alcohol-free fragranced capsules comprising an internal oil-in-water emulsion-type phase comprising a perfume and an external gelified phase.

However, hydrogel beads described in those documents show poor stability in challenging media. Their use in cosmetic, personal care, home care products is therefore very limited.

There is therefore a need to provide a new eco-friendly delivery system that would be stable in a challenging medium such as a consumer product base, with a good performance in terms of active ingredient delivery, e.g. olfactive performance in the case of perfuming ingredients and that could be prepared with a simple process.

The present invention is proposing a solution to the above-mentioned problem, based on a hydrogel bead comprising at least one liquid crystalline structured phase.

SUMMARY OF THE INVENTION

It has now been surprisingly found, that the insertion of at least one liquid crystalline phase (lamellar, hexagonal, cubic or nematic) within a hydrogel bead's matrix reinforced the beads against their dissolution in surfactant-based formulations and creates a creamy texture under deposition on skin or other surfaces without solid residues. Additionally, the solubilisation of a fragrance in such crystalline beads creates a blooming fragrance performance during the deposition on the skin or other surface.

In a first aspect, the present invention relates to a hydrogel bead obtainable by a process comprising the steps of:
(i) preparing a continuous phase comprising water and a biopolymer;
(ii) preparing an internal phase comprising a hydrophobic active ingredient, preferably a perfume oil or a flavor oil,
(iii) mixing the continuous phase and the internal phase to form a dispersion
(iv) forming a bead by inducing complexation of the dispersion obtained in step (iii),
wherein a mesogenic compound is added in step (i) and/or (ii) under conditions that allow the compound to form at least one liquid crystalline structured phase in the hydrogel bead.

In a second aspect, the present invention relates to a hydrogel bead having an internal phase dispersed in a continuous phase, wherein
the internal phase comprises a hydrophobic active ingredient, preferably a perfume oil or a flavor oil; and
the continuous phase comprises a biopolymer and water and forms a hydrogel matrix;
characterized in that the bead comprises at least one liquid crystalline structured phase.

In a third aspect, the invention relates to a process for preparing a hydrogel bead comprising a hydrophobic active ingredient dispersed in a biopolymer matrix, said process comprising the steps of:
(i) preparing a continuous phase comprising water and a biopolymer;
(ii) preparing an internal phase comprising a hydrophobic active ingredient, preferably a perfume oil or a flavor oil,
(iii) Mixing the continuous phase and the internal phase to form a dispersion
(iv) Forming a bead by inducing complexation of the dispersion obtained in step (iii),
wherein a mesogenic compound is added in step (i) and/or (ii) under conditions that allow the compound to form at least one liquid crystalline structured phase in the hydrogel bead.

Another object of the invention is a perfuming composition comprising
(i) hydrogel beads as defined above, wherein the hydrophobic active ingredient comprises a perfume;
(ii) at least one ingredient selected from the group consisting of a perfumery carrier and a perfumery co-ingredient; and
(iii) optionally at least one perfumery adjuvant.

Another object of the invention is a consumer product comprising:
a) from 2 to 65% by weight, relative to the total weight of the consumer product, of at least one surfactant;
b) water or a water-miscible hydrophilic organic solvent; and
c) hydrogel beads or a perfuming composition as defined above.

DETAILED DESCRIPTION OF THE INVENTION

Unless stated otherwise, percentages (%) are meant to designate a percentage by weight of a composition.

The beads of the present invention are crystalline beads. By "crystalline beads" it is meant that the bead comprises at least one liquid crystalline structured phase.

By "Liquid crystalline structured phase", it is meant a phase (lamellar, hexagonal, cubic, nematic) very well organized and having a dense structure with physical properties such as viscosity and permeability, which are intermediate between these of the liquids and the real crystals. The main advantages, making them interesting delivery systems for industrial applications, are their capability to solubilize both hydrophilic and hydrophobic molecules in high quantities.

The presence of anisotropic liquid crystalline phases can be shown by microscopy in cross polarization.

According to a particular embodiment, the liquid crystalline structured phase is chosen in the group consisting of nematic, lamellar, hexagonal and mixtures thereof.

"Liquid crystals (LC)" or "liquid crystalline structured phases" are used indifferently in the present invention.

By "mesogenic compound", it is meant a compound capable of forming liquid crystalline structured phases. A large number of chemical compounds are known to exhibit one or several liquid crystalline phases. These compounds have common features in chemical and physical properties. They are for example slightly soluble in water.

The crystalline bead of the present invention comprises a hydrogel matrix.

Hydrogel beads means that beads are made of three-dimensional network of biopolymer chains and aqueous phase that fills the space between macromolecules. Biopolymers are preferably chosen in the group consisting of alginates, xanthan, carragenans, chitosan, pectin, gellan, agar-agar, hydroxycellulose, hydroxymethylcellulose, hydroxypropyl cellulose, hydroxyethyl celloluse and mixtures thereof.

Crystalline beads of the invention are spherical and have preferably a size between 0.1 mm and 10 mm, preferably between 1 mm and 7 mm.

According to a particular embodiment, beads are macroscopic beads.

By "active ingredient", it is meant a single compound or a combination of ingredients.

By "perfume or flavour oil", it is meant a single perfuming or flavouring compound or a mixture of several perfuming or flavouring compounds.

By "consumer product" or "end-product" it is meant a manufactured product ready to be distributed, sold and used by a consumer.

Figure 1A:
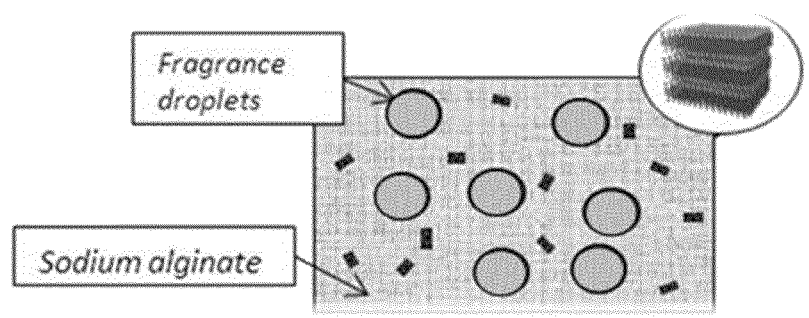
FIG. 1a is a schematic representation of a crystalline bead according to one embodiment of the present invention wherein liquid crystalline structured phases are dispersed in the continuous phase.

A first object of the invention is a hydrogel bead obtainable by a process comprising the steps of:
 (i) preparing a continuous phase comprising water and a biopolymer;
 (ii) preparing an internal phase comprising a hydrophobic active ingredient, preferably a perfume oil or a flavor oil,
 (iii) mixing the continuous phase and the internal phase to form a dispersion
 (iv) forming a bead by inducing complexation of the dispersion obtained in step (iii),
 wherein a mesogenic compound is added in step (i) and/or (ii) under conditions that allow the compound to form at least one liquid crystalline structured phase in the hydrogel bead.

Crystalline beads defined in the present invention comprise an internal phase dispersed in a continuous phase which forms a hydrogel matrix.

Internal Phase Comprising a Hydrophobic Active Ingredient

By "hydrophobic active ingredient", it is meant any hydrophobic active ingredient—single ingredient or a mixture of ingredients—which forms a two-phase dispersion when mixed with water. The hydrophobic active ingredient is liquid at about 20° C.

Hydrophobic active ingredients are preferably chosen from the group consisting of flavor, flavor ingredients, perfume, perfume ingredients, nutraceuticals, cosmetics, pest control agents, biocide actives and mixtures thereof.

According to a particular embodiment, the hydrophobic active ingredient comprises a mixture of a perfume with another ingredient selected from the group consisting of nutraceuticals, cosmetics, pest control agents and biocide actives.

According to a particular embodiment, the hydrophobic active ingredient comprises a mixture of biocide actives with another ingredient selected from the group consisting of perfume, nutraceuticals, cosmetics, pest control agents.

According to a particular embodiment, the hydrophobic active ingredient comprises a mixture of pest control agents with another ingredient selected from the group consisting of perfume, nutraceuticals, cosmetics, biocide actives.

According to a particular embodiment, the hydrophobic active ingredient comprises a perfume.

According to a particular embodiment, the hydrophobic active ingredient consists of a perfume.

According to a particular embodiment, the hydrophobic active ingredient comprises a flavor.

According to a particular embodiment, the hydrophobic active ingredient consists of a flavor.

By "perfume" (or also "perfume oil") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to another embodiment, the hydrophobic active ingredient comprises a flavoring oil.

The term "biocide" refers to a chemical substance capable of killing living organisms (e.g. microorganisms) or reducing or preventing their growth and/or accumulation. Biocides are commonly used in medicine, agriculture, forestry, and in industry where they prevent the fouling of, for example, water, agricultural products including seed, and oil pipelines. A biocide can be a pesticide, including a fungicide, herbicide, insecticide, algicide, molluscicide, miticide and rodenticide; and/or an antimicrobial such as a germicide, antibiotic, antibacterial, antiviral, antifungal, antiprotozoal and/or antiparasite.

As used herein, a "pest control agent" indicates a substance that serves to repel or attract pests, to decrease, inhibit or promote their growth, development or their activity. Pests refer to any living organism, whether animal, plant or fungus, which is invasive or troublesome to plants or animals, pests include insects notably arthropods, mites, spiders, fungi, weeds, bacteria and other microorganisms.

According to any one of the invention's embodiments, the hydrophobic active ingredient represent between about 0.0001% and 50% w/w, or even between 0.01% and 30% w/w, by weight, relative to the total weight of the bead.

According to an embodiment, the internal phase comprises an oil.

According to an embodiment, the internal phase consists of an oil.

According to another embodiment, the internal phase comprises a water-in oil emulsion.

According to an embodiment, the water-in oil emulsion comprises a water phase, an oily phase, an emulsifier and a complexing agent.

According to this embodiment, the emulsifier can be chosen in the group consisting of unsaturated long-chain surfactants such as oleic acid, polyoxyethylene (n) oleyl ethers, sorbitan mono-, di-, trioleate, polyoxyethylene (n) sorbitan mono-, di-, trioleate, glycerol mono-, dioleates, sucrose mono-, di-, trioleate and mixtures thereof.

Preferably, the emulsifier is used in an amount comprised between 0.01 and 50% by weight based on the water-in oil emulsion.

According to an embodiment, the complexing agent is chosen in the group consisting of bivalent electrolytes such as calcium chloride, magnesium chloride and mixtures thereof.

Preferably, the complexing agent is used in an amount comprised between 0.01 and 5% by weight based on the water-in oil emulsion.

The use of water-in oil emulsion (inverse emulsion) comprising a complexing agent as an internal phase allows to deliver complexing agent at the oil—continuous phase interface to create internal membrane protecting the oil from diffusion outside the beads.

According to another embodiment, the internal phase comprises an oil phase dispersed in an encapsulated form and/or in a free form.

According to a particular embodiment, the internal phase consists of a microcapsule slurry.

The encapsulated form can be microcapsules which have been widely described in the prior art, preferably of the core-shell type with a polymeric shell.

The nature of the polymeric shell from the microcapsules of the invention can vary. As non-limiting examples, the shell can be aminoplast-based, polyurea-based or polyurethane-based. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to another embodiment the shell is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another embodiment, the emulsifier is an anionic or amphiphilic biopolymer preferably chosen from the group consisting of gum Arabic, soy protein, gelatin, sodium caseinate and mixtures thereof.

According to another embodiment, the shell is polyurethane-based made from, for example but not limited to polyisocyanate and polyols, polyamide, polyester, etc.

The preparation of an aqueous dispersion/slurry of coreshell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
   A) $C_4$-$C_{12}$ aromatic or aliphatic di- or tri-isocyanates and their biurets, triurets, trimmers, trimethylol propane-adduct and mixtures thereof; and/or
   B) a di- or tri-oxiran compounds of formula
      A-(oxiran-2-ylmethyl)$_n$
      wherein n stands for 2 or 3 and 1 represents a $C_2$-$C_6$ group optionally comprising
      from 2 to 6 nitrogen and/or oxygen atoms;
   v. optionally a $C_1$-$C_4$ compounds comprising two $NH_2$ functional groups;
3) Heating said dispersion;
4) Cooling said dispersion.
This process is described in more details in WO 2013/068255, the content of which is included by reference.

According to another embodiment, the shell of the microcapsule is polyurea- or polyurethane-based. Examples of processes for the preparation of polyurea and polyureathane-based microcapsule slurry are for instance described in WO2007/004166, EP 2300146, EP2579976 the contents of which is also included by reference. Typically a process for the preparation of polyurea or polyurethane-based microcapsule slurry include the following steps:
   a) Dissolving at least one polyisocyanate having at least two isocyanate groups in an oil to form an oil phase;
   b) Preparing an aqueous solution of an emulsifier or colloidal stabilizer to form a water phase;
   c) Adding the oil phase to the water phase to form an oil-in-water dispersion, wherein the mean droplet size is comprised between 1 and 500 µm, preferably between 5 and 50 µm;
   d) Applying conditions sufficient to induce interfacial polymerisation and form microcapsules in form of a slurry.

Continuous Phase Comprising a Biopolymer

As mentioned previously, crystalline beads defined in the present invention comprise an internal phase dispersed in a continuous phase made of at least one biopolymer which forms a hydrogel matrix.

According to an embodiment, biopolymer in the continuous phase is chosen in the group consisting of alginates, xanthan, carragenans, chitosan, pectin, gellan, agar-agar, hydroxycellulose, hydroxymethylcellulose, hydroxypropyl cellulose, hydroxyethyl cellulose and mixtures thereof. These biopolymers are preferred because they are natural, non-toxic products which are completely biodegradable and safe for the environment.

According to a particular embodiment, the continuous phase is made of alginate, preferably sodium alginate, or xanthan.

According to a particular embodiment, the continuous phase represents at least 50% by weight, preferably at least 70% by weight based on the total weight of the bead.

According to a particular embodiment, the amount of biopolymer represents from 0.1 and 10%, preferably from 0.2 and 5% by weight based on the total weight of the bead.

Liquid Crystalline Structured Phases

Crystalline beads according to the invention are characterized by the fact that they comprise at least one liquid crystalline structured phase.

According to an embodiment, the liquid crystalline structured phase is dispersed in the continuous phase.

According to another embodiment, the liquid crystalline structured phase is at the interface between the internal phase and the continuous phase.

According to an embodiment, the liquid crystalline phases is formed by a mesogenic compound chosen in the group consisting of long chain of alcohols (long chain: CH2-groups>12), long chain of fatty acids, long chain of fatty acid salts, long chain of glycerol fatty acids; long chain of lipophilic linear or branched, single or double chained surfactants with HLB<10, long chain of cholesterol esters, polymers and co-polymers having HLB<10 such as diblock, triblock polymers such as the Pluronics.

By "long chain", it means a compound having a hydrocarbon chain of at least 12 carbons.

According to an embodiment, the mesogenic compound is a surfactant having a long hydrocarbon chain of at least 12 carbons and a HLB<10.

According to a particular embodiment, the mesogenic compound selected from the group consisting of glyceryl stearate citrate; sucrose stearate; sucrose distearate; myristil alcohol; palmityl alcohol; stearyl alcohol; oleyl alcohol; behenyl alcohol; lauric acid; myristic acid; palmitic acid; stearic acid; oleic acid; linoleic acid; behenic acid; polyglyceryl-10 myristate; lecithins; mixture of steareth-2 and PEG-8 distearate; glyceryl distearate; ethylene glycol distearate; mixture of Cethet-20 and Glyceryl stearate and PEG-6

Stearate and Steareth-20; mixture of Glyceryl Stearate and Polyglyceryl-6 Palmitate and Cetearyl Alcohol; and mixtures thereof.

One may cite for example commercial products such as Dermofeel GCS, Symbio®muls GC, Symbio®muls WO products of Dr. Straetmans, Nikkomulese LC product of Nikkol Corp., Natragem EW-FL-(MV) product of Croda and mixtures thereof.

According to an embodiment, the mesogenic compound does not comprise cetearyl alcohol combined with benhentrimonium methosulphate.

According to another embodiment, the mesogenic compound does not comprise polyglyceryl diisostearate.

According to an embodiment, beads comprise liquid crystalline phases in an amount comprised between 0.0001% and 70%, preferably between 1% and 50%, more preferably between 3 and 10% based on the total weight of the beads.

Complexation of the dispersion of step (iii) can be obtained according different ways depending on the nature of the biopolymer matrix.

According to a particular embodiment, step (iv) consists of adding the dispersion of step (iii) in a water bath containing water-soluble complexing agent ions, preferably by a drop-by-drop method. This embodiment is particular suitable when the biopolymer is alginate.

According to an embodiment, the water-soluble complexing agent used in step (iv) is selected from the group consisting of calcium, barium, magnesium and in preferably used at a concentration comprised between 0.01 and 5%.

According to another embodiment, step (iv) consists of adding the dispersion of step (iii) in a cold oil bath. This embodiment is particular suitable when the biopolymer is agar.

The amount of water added in step (i) is preferably between 90% and 99%, preferably between 95 and 99%, based on the weight of the dispersion.

The amount of biopolymer added in step (i) is preferably between 0.1% and 10%, preferably between 0.2% and 5%, based on the weight of the dispersion.

The hydrophobic active ingredient is preferably added in an amount comprised between 0.001% and 50%, preferably between 0.01% and 30%, based on the weight of the dispersion.

According to an embodiment, the weight ratio of complexing agents to biopolymer should be between 0.01:1 to 1:0.2.

According to a particular, step (ii) consists of preparing a water-in-oil emulsion.

According to an embodiment, the water-in-oil emulsion is prepared in the presence of an emulsifier and a complexing agent and consists of mixing the aqueous phase, preferably in an amount comprised between 0.001 and 10%, the hydrophobic active ingredient preferably in an amount comprised between 50% and 90%, the emulsifier preferably in an amount comprised between 0.01% and 40% and the complexing agent preferably in an amount comprised between 0.1 and 10% based on the weight of the water-in-oil emulsion until obtaining an homogeneous emulsion.

According to the invention, a mesogenic compound is added in step (i) and/or (ii) under conditions that allow the compound to form liquid crystals.

The amount of mesogenic compound added in step (i) and/or (ii) is preferably between 0.0001% and 50%, preferably between 0.001% and 30%, based on the weight of the dispersion.

It is well-known that liquid crystals can be produced through modification of physical parameters such as concentration or temperature.

The person skilled in the art will be able to select suitable conditions for forming liquid crystals depending on the nature of the mesogenic compound.

As an example, the solution containing the liquid crystal phase can be heated, for example at a temperature comprised between 40° C. and 70° C. followed by a cooling, for example at room temperature, to facilitate the liquid crystalline phase formation.

When the mesogenic compound is added in step (i) (i.e in the aqueous phase), crystalline beads prepared by the process comprises liquid crystals dispersed in the continuous phase whereas when the mesogenic compound is added in step (ii) (i.e in the oily phase), crystalline beads prepared by the process comprise liquid crystals at the interface between the dispersed phase and the continuous phase (i.e around the oil droplets).

Indeed, due to the poor solubility of the mesogenic compound in water, when added step (ii), liquid crystals are formed at the interface between the continuous phase and the internal phase once the two phases are mixed.

According to a particular embodiment, the process comprises further step consisting of adding the dispersion to a hydrophobic solvent such as ethyl citrate, silicon oils, Neobee, isopropyl myristate to form a reverse emulsion between step (iii) and step (iv) and a further step consisting of removing the hydrophobic solvent by dilution after step (iv).

According to an embodiment, beads as defined in the present invention are in the form of a consumer product, for example in the form of a personal care product such as a shower gel or a body lotion and can be used as such by a consumer. According to this embodiment, beads can be suspended in water or in a biopolymer gel for example made of water, xanthan gum and potassium sorbate or in any cosmetic gel.

According to this embodiment, the hydrogel matrix and/ or the internal phase can comprise a consumer product base ingredients including components chosen in the group consisting of surfactants, thickening polymers, pigments, UV filters, aesthetic particles, emollients, hydrating agents, antimicrobial agents, bioactives, preservatives, preferably in an amount up to 50%, preferably up to 20% based on the total weight of the continuous phase.

Another object of the invention is a process for preparing a hydrogel bead comprising a hydrophobic active ingredient dispersed in a biopolymer matrix, said process comprising the steps of:
  (i) preparing a continuous phase comprising water and a biopolymer;
  (ii) preparing an internal phase comprising a hydrophobic active ingredient, preferably a perfume oil or a flavor oil,
  (iii) Mixing the continuous phase and the internal phase to form a dispersion
  (iv) Forming a bead by inducing complexation of the dispersion obtained in step (iii),
wherein a mesogenic compound is added in step (i) and/or (ii) under conditions that allow the compound to form at least one liquid crystalline structured phase in the hydrogel bead.

All of the embodiments described for the hydrogel beads above also apply for the process for preparing hydrogel beads.

Another object of the invention is a hydrogel bead having an internal phase dispersed in a continuous phase, wherein the internal phase comprises a hydrophobic active ingredient, preferably a perfume oil or a flavor oil; and
the continuous phase comprises a biopolymer and water and forms a hydrogel matrix;
characterized in that the crystalline bead comprises at least one liquid crystalline structured phase.

Crystalline beads defined in the present invention comprise an internal phase dispersed in a continuous phase which forms a hydrogel matrix.

According to a particular embodiment, the continuous phase represents at least 50% by weight, preferably at least 70% by weight based on the total weight of the bead.

According to a particular embodiment, the amount of biopolymer represents from 0.1 and 10%, preferably from 0.2 and 5% by weight based on the total weight of the bead.

According to an embodiment, beads comprise liquid crystalline phases in an amount comprised between 0.0001% and 70%, preferably between 1% and 50%, more preferably between 3 and 10% based on the total weight of the beads.

All of the embodiments described above also apply for the hydrogel beads.

Another object of the invention is a perfuming composition comprising beads as defined previously, at least one ingredient selected from the group consisting of perfuming co-ingredients, a perfumery carrier and mixtures thereof, and optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

The invention's crystalline beads can advantageously be used in different fields of perfumery, i.e. fine or functional perfumery.

Consequently, another object of the present invention is represented by a consumer product, preferably a perfuming consumer product comprising the crystalline beads as defined above.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. These formulations do not warrant a detailed description here which would in any case not be exhaustive. The person skilled in the art of formulating such consumer products is perfectly able to select the suitable components on the basis of his general knowledge and of the available literature.

In particular, examples of such formulations can be found in the patents and patent applications relative to such products, for example in WO2008/016684, US2007/0202063, WO2007/062833, WO2007/062733, WO2005/054422, EP1741775, GB2432843, GB2432850, GB2432851, GB2432852, WO 9850011, WO2013174615 or WO2012084904.

Non-limiting examples of suitable perfumery consumer product can be a perfume, such as a fine perfume, a body splash, a cologne or an after-shave lotion; a fabric care product, such as a liquid detergent, a fabric softener, a fabric refresher, an ironing water, or a bleach; a body-care product, such as a hair care product (e.g. a shampoo, hair conditioner, a coloring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener; or a home care product, such all-purpose cleaners, liquid dishwashing products, toilet cleaners or products for cleaning various surfaces, for example sprays & wipes intended for the treatment/refreshment of textiles or hard surfaces (floors, tiles, stone-floors etc.).

According to an embodiment, the perfuming consumer product is in the form of a personal care product, for example in the form of a shower gel or a body lotion.

The beads of the invention when encapsulating a flavour, can also be used in a great variety of edible end products. Consumer products susceptible of being flavoured by the microcapsules of the invention may include foods and beverages. For example foodstuff base that could use the powdered microcapsules of the invention include Non-alcoholic beverages (e.g. carbonated soft drinks, bottled waters, sports/energy drinks, juice drinks, vegetable juices, vegetable juice preparations), Alcoholic beverages (e.g. beer and malt beverages, spirituous beverages), Milk products (e.g. fresh cheese, soft cheese, hard cheese, milk drinks, whey, butter, partially or wholly hydrolysed milk protein-containing products, fermented milk products, condensed milk and analogues), Dairy based products (e.g. fruit or flavored yoghurt, ice cream, fruit ices)

Chocolate and compound coatings

Products based on fat and oil or emulsions thereof (e.g. mayonnaise, spreads, margarines, shortenings, remoulade, dressings, spice preparations), Desserts (e.g. gelatins and puddings)

Products made of soya protein or other soya bean fractions (e.g. soya milk and products made therefrom, soya lecithin-containing preparations, fermented products such as tofu or tempeh or products manufactured therefrom, soya sauces), Vegetarian meat replacer, vegetarian burger Spices or spice preparations (e.g. mustard preparations, horseradish preparations), spice mixtures and, in particular seasonings which are used, for example, in the field of snacks.

Crystalline beads defined in the present invention have proven to have a pleasant texture while being particularly and advantageously stable in challenging medium.

The invention will now be further described by way of examples. It will be appreciated that the invention as claimed is not intended to be limited in any way by these examples.

EXAMPLES

Example 1

Alginate Perfumed Beads Containing a Liquid Crystalline Structured Phase Dispersed in the Continuous Phase In a first step, a suspension of liquid crystals in an alginate solution was prepared (phase A). Glyceryl stearate citrate (Dermofeel GSC) was added in alginate solution and heat to 65° C. under stirring in water bath. After cooling phase A to room temperature, the fragrance (phase B) was added and the mixture was agitated with a stirring motor RW 11 basic "Lab egg" IKA with paddle stirrer R1001 (d=34 mm) at 500/600 rpm for 5/10 min.

The second step consists forming spherical beads in a calcium solution (phase C). Alginate solution containing liquid crystals and fragrance was added drop by drop in a water bath containing calcium ions.

Figure 1B:
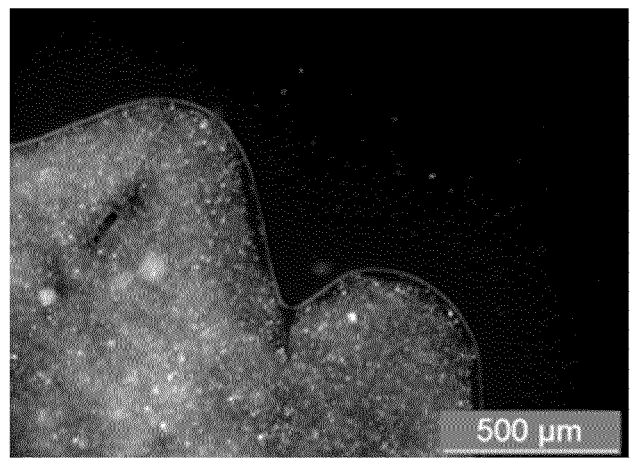
FIG. 1b represents microscopic image of the hydrogel matrix obtained in example 1 observed under microscope in polarized light.
Figure 2:
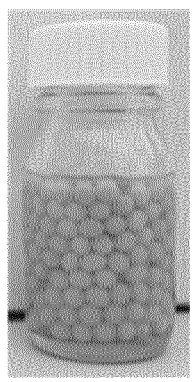
FIG. 2 represents crystalline beads of the present invention.

After 20 minutes in contact with calcium solution, beads comprising liquid crystalline phases dispersed in the continuous phase (i.e hydrogel matrix) are obtained (see FIGS. 1a and 1b where liquid crystalline phases can be seen in polarized light). Then, they were filtered, washed 3 times and placed in water (see FIG. 2). The obtained beads show a creamy texture.

TABLE 1

Composition of the different phases involved during the process

| | Ingredient | Function | % wt |
|---|---|---|---|
| Phase A Continuous phase | Sodium Alginate [1] (2% wt in water) | Biopolymer | 54.90 |
| | Dermofeel GSC [2] | Mesogenic compound | 2.88 |
| | Water | Aqueous phase | 42.22 |
| Phase B Internal phase | Fragrance A [3] | Hydrophobic active ingredient | 100 |
| Phase C | CaCl$_2$ (0.5% wt in water) | Complexing agent | 100 |

TABLE 2

Final composition of alginate beads containing liquid crystals (LC dispersed in the continuous phase)

| Ingredient | % wt |
|---|---|
| Sodium Alginate [1] (2% wt in water) | 54.63 |
| Dermofeel GSC[2] | 2.87 |
| Fragrance A [3] | 0.5 |
| Water | 42 |
| Total | 100 |

[1] Origin: Alfa Aesar, Karlsruhe, Germany
[2] Glyceryl stearate citrate, Origin: Dr Straetmans GmbH, Hambourg, Germany
[3] See table 2a TABLE 2a Composition of fragrance A

| Raw mat | % in formula |
|---|---|
| STIRRALLYL ACETATE | 4.5% |
| BENZYL ACETATE | 0.9% |
| ALDEHYDE C10 | 2.1% |
| HEXYLCINNAMIC ALDEHYDE | 14.3% |
| ALLYL CAPROATE | 0.7% |
| Ethyl 2-methyl-pentanoate | 0.9% |
| BENZYL BENZOATE | 35.3% |
| CITRONELLYL NITRILE | 1.8% |
| CORANOL [1] | 5.4% |
| DIHYDROMYRCENOL | 5.4% |
| FRUCTALATE ® [2] | 5.4% |
| HEDIONE ® [3] | 14.9% |
| LIMONENE | 2.4% |
| LINALOOL | 1.0% |
| METHYL METHYLANTHRANILATE | 1.5% |
| PARACYMENE | 1.7% |
| RHUBOFLOR | 0.7% |
| TERPINENE G | 0.6% |
| 2,4-Dimethyl-3-cyclohexene-1-carbaldehyde | 0.6% |
| TOTAL | 100% |

[1] 4-cyclohexyl-2-methyl-2-butanol; origin and Trademark from Firmenich SA, Geneva, Switzerland
[2] 1,4-cyclohexane dicarboxylate de diéthyle; origin and Trademark from Firmenich SA, Geneva, Switzerland
[3] Methyl dihydrojasmonate; origin and Trademark from Firmenich SA, Geneva, Switzerland

Example 2

Alginate Perfumed Beads Containing a Liquid Crystalline Structured Phase and Inverse Emulsion The internal phase used in this example consists of an inverse emulsion (water-in-oil emulsion) comprising a complexing agent contrary to example 1 where the internal phase consists only of an oil phase.

The method comprises the following steps:
1) The first step is the preparation of an inverse emulsion containing fragrance, emulsifier and water with complexing agents. All ingredients were added one after another and mixed until complete dissolution at RT (an ultra turrax can be used).
2) After biopolymer dissolution in water, the mesogenic compound is added in this solution in order to form liquid crystalline phases. It is possible to heat this solution for facilitate the liquid crystalline phase formation.
3) The inverse emulsion is added to the biopolymer solution containing LC (at RT). The mixture is strongly mixed. Microparticles containing w/o emulsion are formed in the biopolymer solution.
4) The last step consists to form spherical beads in aqueous solution of complexing agents by adding drop by drop the mixture obtained in step 3) in it.
5) After their formation, spherical particles are removed from the complexing agents solution, washed 3 times and placed in water.

TABLE 3

Composition of the different phases involved during the process

|  | Ingredient | Function | % wt |
|---|---|---|---|
| Phase A Internal phase | Fragrance[1] | Hydrophobic active ingredient | 76 |
|  | Brij 93[2] | Emulsifier | 5 |
|  | Aminat G [3] (20% wt in water) | Complexing agent | 19 |
| Phase B Continuous phase | Sodium Alginate [4] (0.5% wt in water) | Biopolymer | 95 |
|  | Dermofeel GSC [5] | Mesogenic compound | 5 |
| Phase C | CaCl$_2$ (1% wt in water) | Complexing agent | 100 |

[1] see table 2A
[2] Polyoxyethylene (2) oleyl ether
[3] Ethyl Lauroyl Arginate HCl; Origin: Vedeqsa Inc, Spain
[4] Origin: Alfa Aesar, Karlsruhe, Germany
[5] Glyceryl stearate citrate, Origin: Dr Straetmans GmbH, Hambourg, Germany

TABLE 4

Final Composition of the perfumed beads

| Ingredient | % wt |
|---|---|
| Fragrance [1] | 7.6 |
| Brij 93[2] | 0.5 |
| Aminat G [3] (20% wt in water) | 1.9 |
| Sodium Alginate [4] (0.5% wt in water) | 85.5 |
| Dermofeel GSC [5] | 4.5 |
| Total | 100 |

[1] see table 2A
[2] Polyoxyethylene (2) oleyl ether
[3] Ethyl Lauroyl Arginate HCl; Origin: Vedeqsa Inc, Spain
[4] Origin: Alfa Aesar, Karlsruhe, Germany
[5] Glyceryl stearate citrate, Origin: Dr Straetmans GmbH, Hambourg, Germany Example 3 (Comparative Example)

Alginate Perfumed Beads without Liquid Crystals

In a first step, an alginate solution was prepared (phase A). Then, the fragrance (phase B) was added and the mixture was agitated with a stirring motor RW 11 basic "Lab egg" IKA with paddle stirrer R1001 (d=34 mm) at 500/600 rpm for 5/10 min.

The second step consists forming spherical beads in a calcium solution (phase C). Alginate solution and fragrance was added drop by drop in a water bath containing calcium ions.

TABLE 5

Composition of the different phases involved during the process

|  | Ingredient | Function | % wt |
|---|---|---|---|
| Phase A Continuous phase | Sodium Alginate [1] (1.46% wt in water) | Biopolymer | 100 |
| Phase B Internal phase | Fragrance [2] | Hydrophobic active ingredient | 100 |
| Phase C | CaCl$_2$ (1% wt in water) | Complexing agent | 100 |

[1] Origin: Alfa Aesar, Karlsruhe, Germany
[2] see table 2A

TABLE 6

Final composition of perfumed beads (without liquid crystalline phase)

|  | Ingredient | % wt |
|---|---|---|
| Phase A | Sodium Alginate [1] (1.46% wt in water) | 92.5 |
| Phase B | Fragrance [2] | 7.5 |

[1] Origin: Alfa Aesar, Karlsruhe, Germany
[2] see table 2A

Example 4

Alginate Perfumed Beads Containing Liquid Crystalline Structured Phase (at the Interface Between the Continuous Phase and the Internal Phase)

This type of beads is prepared from a direct oil-in-water (o/w) emulsion composed of an aqueous phase (phase A) and an oily phase containing a fragrance (phase B). The principal difference with the previous beads from example 1 is the location of the LC; they cover the fragrance droplets instead of being dispersed in alginate phase.

In a first step, the two phases A and B are heated up to 50° C. in order to dissolve the mesogenic compound in the fragrance. The emulsion is obtained by mixing A and B under mechanical stirring with stirring motor RW 11 basic «Lab egg» and paddle type stirrer: 1500 rpm during 15 minutes at room temperature.

The second step consists forming spherical beads in a calcium solution (phase C). Alginate solution and fragrance containing liquid crystals were added drop by drop in a water bath containing calcium ions.

Figure 3A:
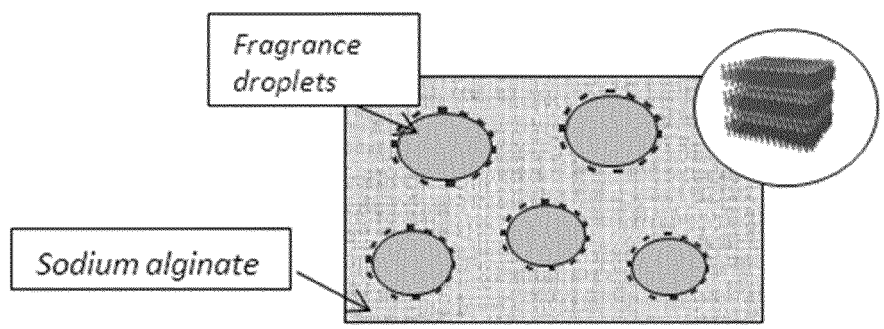
FIG. 3a is a schematic representation of the crystalline beads according to another embodiment of the present invention wherein liquid crystalline structured phases are located at the interface between the internal phase and the continuous phase.
Figure 3B:
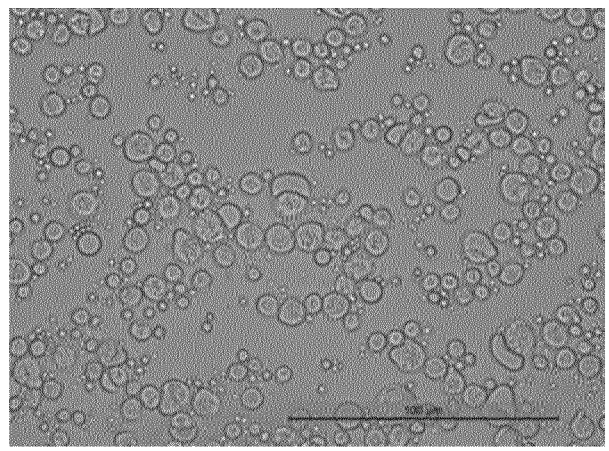
FIG. 3b represents microscopic image of the hydrogel matrix obtained in example 4 observed under microscope in transmitted light.
Figure 3C:
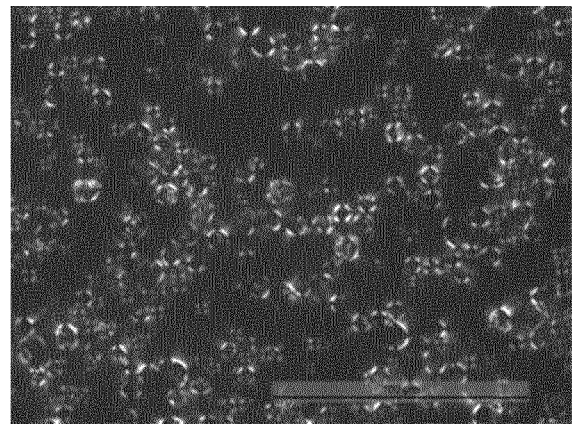
FIG. 3c represents microscopic image of the hydrogel matrix obtained in example 4 observed under microscope in polarized light.

After 20 minutes in contact with calcium solution, beads comprising liquid crystalline phases at the interface between the internal phase and the continuous phase are obtained (see FIG. 3b where liquid crystalline phases can be seen in polarized light).

TABLE 7

Composition of the different phases involved during the process

|  | Ingredient | Function | % wt |
|---|---|---|---|
| Phase A Continuous | Sodium Alginate [1] Water | Biopolymer Aqueous phase | 1.14 98.9 |

TABLE 7-continued

Composition of the different phases involved during the process

| | Ingredient | Function | % wt |
|---|---|---|---|
| phase | | | |
| Phase B Internal phase | Fragrance [2] | Hydrophobic active ingredient | 50 |
| | Natragem™ EW 3) | Mesogenic compound | 50 |
| Phase C | CaCl$_2$ (1% wt in water) | Complexing agent | 100 |

[1] Origin: Alfa Aesar, Karlsruhe, Germany
[2] see table 2A
3) Glyceryl Stearate (and) Polyglyceryl-6 Palmitate/Succinate (and) Cetearyl Alcohol Origin: Croda Inc.

TABLE 8

Final composition of the crystalline perfumed beads (LC at the interface between the internal phase and the continuous phase)

| Ingredient | % wt |
|---|---|
| Sodium Alginate | 1 |
| Water | 87 |
| Fragrance | 6 |
| Natragem™ EW | 6 |
| Total | 100 |

Example 5

Agar Perfumed Beads Containing Liquid Crystalline Structured Phase

In a first step, a solution was prepared using the ingredients in phase A (in Table 9 below). Then, an inverse emulsion was prepared using the ingredient in phase B. All compounds were added and mixed to form this W/O emulsion. Next, phase B was added to phase A to form a dispersion. Said dispersion was heated to boiling (90° C.).

The second step is to form spherical beads in oil (phase C). The dispersion (phases A+B) was adding drop by drop in a cold oil bath (10° C.).

After 5 minutes in phase C, beads obtained were removed.

TABLE 9

Composition of the different phases involved during the process

| | Ingredient | Function | % wt |
|---|---|---|---|
| Phase A Continuous phase | Water | Aqueous phase | 86.21 |
| | Agar agar [1] | Biopolymer | 0.86 |
| | Dermofeel GSC | Mesogenic compound | 4.31 |
| Phase B Internal phase | Fragrance | Hydrophobic active ingredient | 1.64 |
| | Aminat-G (20% wt in water)[2] | Complexing agent | 6.55 |
| | Brij 93 | Emulsifier | 0.43 |
| Phase C | Oil | Complexing medium | 100 |

[1] Origin: AppliChem GmbH
[2] Origin: Vedeqsa Inc, Spain

TABLE 10

Final composition: of the crystalline perfumed beads

| Ingredient | % wt |
|---|---|
| Water | 86.21 |
| Agar agar | 0.86 |
| Dermofeel GSC | 4.31 |
| Fragrance | 1.64 |
| Aminat-G (20% wt in water) | 6.55 |
| Brij 93 | 0.43 |
| Total | 100 |

Example 6

Shower Gel in the Form of Crystalline Alginate Perfumed Beads

In the first stage, the first 5 compounds of phase A representing an example of personal care formulation are mixed together.

In a second stage, an alginate solution is prepared with the compounds 6 and 7 of the continuous phase: alginate solution and dermofeel GSC in the given proportion. Dermofeel GSC and alginate hydrogel are stirred at 65° C. for 1 h. Then, the sample is cooled down under stirring to reach room temperature.

Finally, the obtained mixture of phase A and phase B are agitated with a stirring motor RW 11 basic "Lab egg" IKA with paddle stirrer R1001 (d=34 mm) at 500/600 rpm for 5-10 min at room temperature.

In the final stage the crystalline beads are formed by prilling the mixture of phases A and B in 0.5% CaCl$_2$ aqueous solution. Once the beads are created, they are filtered, washed 3 times with distilled water and kept in water or in water with a desired thickener such as a biopolymer or other polymer used for this purpose.

Crystalline beads prepared by the process described in this example can be used as such by the consumer as a shower gel.

TABLE 11

Composition of the different phases involved during the process

| | | Ingredient | % wt |
|---|---|---|---|
| Phase A Continuous phase | 1 | Water | 16.95 |
| | 2 | [1]Carbopol ® Aqua SF1 | 3.68 |
| | 3 | [2]Texapon N70 - 26.36% | 12.89 |
| | 4 | NaOH @ 20% | 0.37 |
| | 5 | [3]Tego ® Betain F50 | 2.95 |
| | 6 | Sodium Alginate (2% in DI-Water) | 60.00 |
| | 7 | Dermofeel GSC | 3.16 |
| Phase B Internal phase | | Fragrance [4] | 100 |
| Phase C | | CaCl$_2$ (1% wt water) | 100 |

[1] Acrylates Copolymer; Origin: Lubrizol Corp.
[2] Sodium Laureth Sulfate; Origin: BASF
[3] Cocamidopropyl Betaine; Origin: Evonik Industries
[4] See table 2A

TABLE 12

Final composition of the shower gel crystalline beads

| Ingredient | % wt |
| --- | --- |
| Water | 16.10 |
| Carbopol Aqua SF1 | 3.50 |
| Texapon N70 - 26.36% | 12.25 |
| NaOH @ 20% | 0.35 |
| Tego Betain F50 | 2.80 |
| Fragrance [3] | 5 |
| Sodium Alginate @ 2% | 57 |
| Dermofeel GSC | 3 |
| Total | 100 |

Example 7

Body Lotion in the Form of Crystalline Alginate Perfumed Beads

Phase A: Continuous phase

| Name | Ingredient | Function | % wt |
| --- | --- | --- | --- |
| | Sodium Alginate [1] | Biopolymer | 0.51 |
| | Propylene Glycol | Humectant | 2.56 |
| | Carbopol Aqua SF | Stabiliser | 1.86 |
| PNC 400 | Sodium carbomer | Stabiliser | 0.10 |
| | Water | Solvent | 88.46 |
| Arlacel 985 | Steareth-2 (AND) PEG-8 Distearate | Mesogenic compound | 2.56 |
| | Cetyl Alcohol | Mesogenic compound | 0.26 |
| Tefose 2561 | Cethet-20 (and) Glyceryl stearate (and) PEG-6 Stearate (and) Steareth - 20 | Mesogenic compound | 2.05 |
| | Dermofeel GSC [2] | Mesogenic compound | 1.33 |
| Nipaguard PO 5 | Phenoxyethanol (and) Pyroctone olamin | Preservative | 0.31 |

Phase B: internal phase

| Name | Ingredient | Function | % wt |
| --- | --- | --- | --- |
| Biolip P 90 | Squalan | Emollient | 7.90 |
| Mineral oil 30-40 cp | Paraffin oil | Emollient | 15.81 |
| Petroleum jelly | Petrolatum | Emollient | 43.46 |
| | Fragrance A | Hydrophobic active ingredient | 32.83 |
| Phase C | CaCl$_2$ (0.5% wt in water) | Complexing agent | 100 |

TABLE 13

Final composition of body lotion crystalline beads

| Final Composition | % wt |
| --- | --- |
| Alginate | 0.48 |
| Propylene Glycol | 2.41 |
| carbopol | 1.75 |
| Sodium carbomer | 0.10 |
| Water DI | 83.07 |
| Phenoxyethanol (and) Pyroctone olamin | 0.29 |
| Dermofeel SGC | 1.25 |
| Steareth-2 (AND) PEG-8 Distearate | 2.41 |
| Cetyl Alcohol | 0.24 |
| Cethet-20 (and) Glyceryl stearate (and) PEG-6 Stearate (and) Steareth - 20 | 1.93 |

TABLE 13-continued

Final composition of body lotion crystalline beads

| Final Composition | % wt |
| --- | --- |
| Squalan | 0.48 |
| Paraffin oil | 0.96 |
| Petrolatum | 2.65 |
| Fragrance | 2.00 |
| Total | 100.00 |

Process of Preparation:

I. Preparing the phase A by mixing a NaAlginate 2% wt in water solution with the Carbopol Aqua SF 7% in water with all the remaining components of phase A. The mixture is heated to 67° C. under agitation at 600 rpm and cooled down to room temperature to form the liquid crystals.

II. Preparing phase B
Mixing of all compounds to obtain a homogeneous mixture

III. Mixing phase A and phase B under stirring at 500 rpm during 1 hour at room temperature IV. The crystalline beads are formed by prilling the mixture of phases A and B in 0.5% CaCl$_2$ aqueous solution.

V. The beads are rinsed and stored in a water or in a gel having the following composition:

| Ingredients | % wt |
| --- | --- |
| Keltrol TF (xanthan gum) | 0.6 |
| water | 99.22 |
| Potassium sorbate | 0.18 |

Example 8

Fragrance Release Performance

The perfume release from solutions containing phases A and B as defined in example 2 (sample A), before the formation of spherical beads in calcium, were measured by gas chromatography combined with mass spectroscopy analysis at temperature 37° C. and was compared with the perfume release from solutions containing phases A and B as defined in example 3 (comparative B).

The perfume leakage is measured by extraction of the water phase, in which the crystalline hydrogel beads are stored and analyzing by using GC-MS instrument.

For analysis, 5 g of sample and 5 ml of ISTD (internal standard compound) solution are used. This sample is agitated with the IKA incubator for 10 min at 400 rpm then centrifuged 5 min at 5000 rpm. Then 1.5 ml are injected in GC-MS instrument.

An Agilent GC with a split/splitless inlet and Helium as carrier gas are used. The samples are analysed with a split ratio 10:1. The analyses are performed at constant flow with an initial flow rate at 1 mL/min (corresponding to an average velocity of 37 cm/s). The oven program starts at 80° C.; a first ramp temperature at 10° C./min attains 200° C., followed by another one at 20° C./min to reach 260° C. This final temperature is held for 1 min.

The GC-MS equipment allows working in SIM analysis: 2 or 3 ions per compounds are chosen and analysed on the gas chromatogram after a solvent delay of 2 min.

The perfume release was determined for 2 perfumery raw materials: benzyl acetate and dihydromyrcenol. The release from comparative sample B is taken as 100%

Figure 4A:
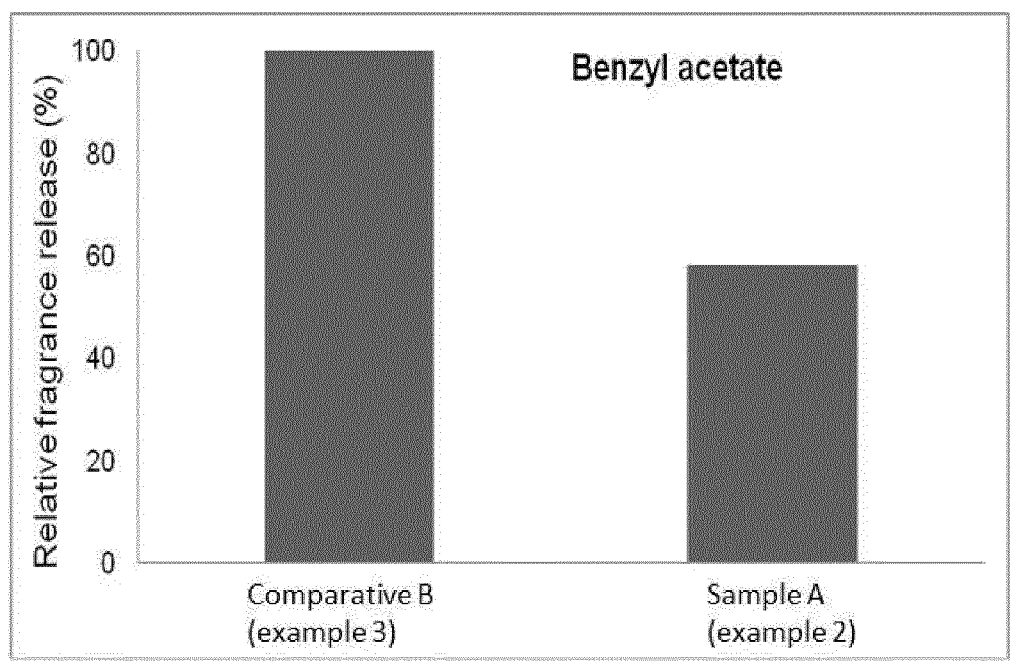
FIG. 4 represent the fragrance release performance (FIG. 4a for benzyl acetate and FIG. 4b for dihydromyrcenol).
Figure 4B:
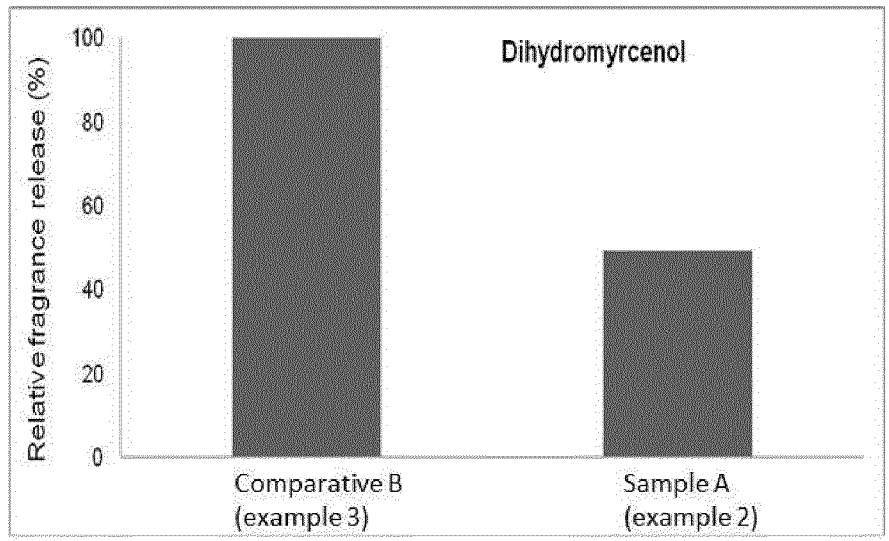

Results are shown on FIGS. 4a and 4b.

One can conclude from those figures that the crystalline beads according to the invention lead to a better retention of the fragrance into the beads compared to the comparative sample B devoid of liquid crystals since a lower gas concentration of fragrance is observed for sample A (according to the invention).

Example 9

Mechanical Properties

Figure 5:
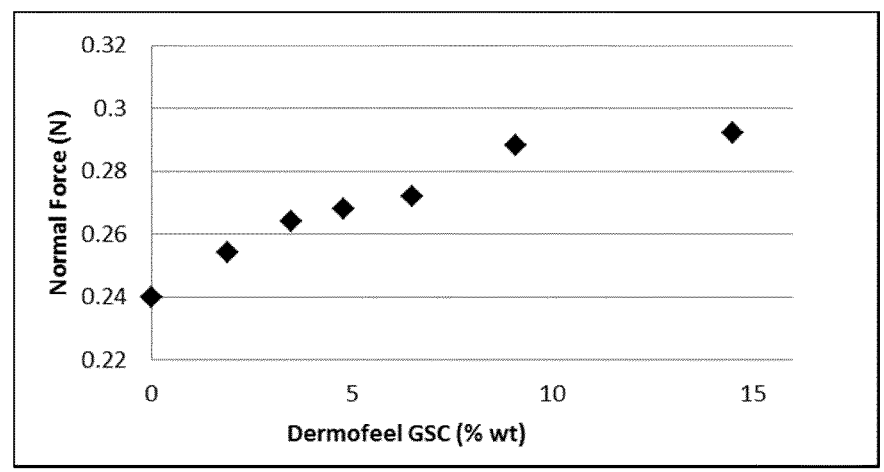
FIG. 5 represents normal force as function of the concentration of the mesogenic compound in a crystalline bead according to the invention.

The influence of liquid crystalline (LC) phases on the rigidity of the beads was investigated by measuring the normal force necessary to deform the alginate particles prepared according to example 2. Texture Analyser TA-XT2 was used for this purpose. The normal force as function of the concentration of the mesogenic compound (Dermofeel GSC) is presented on FIG. 5.

One can conclude from this example that the beads are reinforced by the presence of LC phases because the normal force for deformation is higher than in the absence of LC phases.

Example 10

Alginate Beads Containing Liquid Crystalline Structured Phase Dispersed in the Continuous Phase and Core-Shell Microcapsules In a first step, a suspension of liquid crystals in an alginate solution was prepared (phase A). Glyceryl stearate citrate (Dermofeel GSC) was added in alginate solution and heat to 65° C. under stirring in water bath. After cooling phase A to room temperature, the capsules slurry (phase B) was added and the mixture was agitated with a stirring motor RW 11 basic "Lab egg" IKA with paddle stirrer R1001 (d=34 mm) at 500/600 rpm for 5/10 min.

The second step consists forming spherical beads in a calcium solution (phase C). Alginate solution containing liquid crystals and fragrance was added drop by drop in a water bath containing calcium ions.

After 5 minutes in contact with calcium solution, beads comprising liquid crystalline phases dispersed in the continuous phase (i.e hydrogel matrix) are obtained. Then, they were filtered, washed 3 times and placed in water. The obtained beads show a creamy texture.

TABLE 14

Composition of the different phases involved during the process

|  | Ingredient | Function | % wt |
|---|---|---|---|
| Phase A Continuous phase | Water | Aqueous phase | 88 |
|  | Dermofeel GSC[2] | Mesogenic compound | 10 |
|  | Sodium Alginate | Biopolymer | 2 |
| Phase B Internal phase | Capsule slurry[3] | Hydrophobic active ingredient | 100 |
| Phase C | CaCl$_2$ (0.5% wt in water) | Complexing agent | 100 |

TABLE 15

Final composition of alginate beads containing liquid crystals and core-shell microcapsules

| Ingredient | % wt |
|---|---|
| Sodium Alginate | 1.8 |
| Dermofeel GSC[2] | 4.5 |
| Capsule slurry[3] | 10 |
| Water | 83.7 |
| Total | 100 |

[2] Glyceryl stearate citrate, Origin: Dr Straetmans GmbH, Hamburg, Germany.
[3] see below process for preparing the microcapsules slurry.

Preparation of Melamine Glyoxal Microcapsules Coated with Cationic Polymers

In a round bottom flask, melamine (0.87 g), 2,2-dimethoxyethanal (60 wt % in water, 1.32 g), glyoxal (40 wt % in water, 1.66 g) and glyoxylic acid (50 wt % in water, 0.56 g) were dispersed in water (1.53 g) at RT. The pH value of the dispersion was controlled with sodium hydroxide (30 wt % in water, pH=9.5). The reaction mixture was heated at 45° C. for 25 minutes to give a solution. Then water (6.50 g) was added and the resin was stirred at 45° C. for 5 min.

Resin was transferred in a 200 mL beaker. Guanazole (0.58 g) was dissolved in a solution of Ambergum 1221 (2 wt % in water, 24.86 g). The resulting solution was introduced into the beaker. An oil solution of Takenate D-110N (2.07 g), perfume B (24.72 g)—see table b) below and Uvinul A plus (1.41 g) was added into the aqueous solution. The biphasic reaction mixture was sheared with an Ultra-turrax at 21500 rpm for 2 min. Acetic acid was added to initiate the polycondensation (pH=5.35). The quality of the emulsion was controlled by light microscopy. The emulsion was transferred into a 200 mL Schmizo reactor and was heated at 45° C. for 1 h, then at 60° C. for 1 h and finally at 80° C. for 2 h. Varied amounts of a solution of first cationic copolymer namely acrylamidopropyltrimonium chloride/acrylamide copolymer (Salcare® SC60, origin BASF) (3 wt % in water), and second cationic copolymer polygalactomannan 2-hydroxy propyltrimethylammonium chloride ether (Jaguar C13S, origin Rhodia) (1 wt % in water), were then added and the reaction mixture was heated at 80° C. for 30 min. A solution of urea (4.90 g, 40 wt % in water) was finally added to the reaction mixture, which was heated at 80° C. for 30 min.

TABLE b

Composition of perfume B

| Ingredient | % in oil |
|---|---|
| Verdyl acetate | 17.5 |
| Eucalyptol | 16.7 |
| Dihydromyrcenol | 11.1 |
| Benyl Benzoate | 9.4 |
| Alpha terpinyl acetate | 6.6 |
| Nopyl acetate | 4.9 |
| Verdox® [1] | 4.2 |
| Anethol | 4.1 |
| Veloutone® [2] | 3.0 |
| Methyl hexyl ketone | 2.9 |
| Borneol | 2.8 |
| Gamma terpinyl acetate | 2.3 |
| Ethyl amyl ketone | 2.1 |
| Ethyl pentyl ketone | 1.8 |
| Gamma undecalactone | 1.8 |
| Patchouli alcohol | 1.7 |
| Isoborneol | 1.6 |

TABLE b-continued

Composition of perfume B

| Ingredient | % in oil |
|---|---|
| Camphor | 1.0 |
| Cyclogalbanate ® [3] | 0.9 |
| Alpha guaiene | 0.8 |
| Rose oxide | 0.8 |
| Dihydrocarvyl acetate | 0.8 |
| Alpha bulnesene | 0.6 |
| Aldehyde C12 | 0.6 |
| TOTAL | 100.00 |

[1] Trademark from IFF; 2-tert-butyl-1-cyclohexyl acetate
[2] Trademark from Firmenich; 2,2,5-trimethyl-5-pentylcyclopentan-1-one
[3] Trademark from Symrise; galbanum oxyacetate Example 11

Refreshing Beads for Oral Care

In a first step, a suspension of liquid crystals in alginate solution was prepared (phase A). To prepare this solution, sucrose was added into water. After homogenization, sodium alginate was added and the solution was mixed until homogeneous. Sugar Ester Ryoto S-970 was added in the alginate solution. The mixture was heated to 75° C. under stirring in water bath. After cooling phase A to room temperature, the flavour (phase B) was added and the mixture was agitated with a stirring motor RW 11 basic "Lab egg" IKA with paddle stirrer R1001 (d=34 mm) at 500/600 rpm for 10 min.

The second step consists in forming spherical beads in a calcium solution (phase C). Alginate solution containing liquid crystals and fragrance was added drop by drop in a water bath containing calcium ions.

After 10 minutes in contact with calcium solution, beads comprising liquid crystalline phases dispersed in the continuous phase (i.e hydrogel matrix) are obtained. Then, they were filtered, washed 3 times and placed in water. The obtained beads show a creamy texture.

TABLE 16

Composition of the different phases involved during the process

| | Ingredient | Function | % wt |
|---|---|---|---|
| Phase A Continuous phase | Water | Aqueous phase | 80.1 |
| | Sucrose [1] | Sugar | 9 |
| | Sodium Alginate [2] | Biopolymer | 0.9 |
| | Sugar Ester Ryoto S-970 [3] | Mesogenic compound | 10 |
| Phase B Internal phase | Mint flavor [4] | Hydrophobic active ingredient | 100 |
| Phase C | CaCl$_2$ (0.5% wt in water) | Complexing agent | 100 |

TABLE 17

Final composition of refreshing alginate beads containing liquid crystals (LC dispersed in the continuous phase)

| Ingredient | % wt |
|---|---|
| Sucrose [1] | 8.96 |
| Sodium Alginate [2] | 0.89 |

TABLE 17-continued

Final composition of refreshing alginate beads containing liquid crystals (LC dispersed in the continuous phase)

| Ingredient | % wt |
|---|---|
| Sugar Ester Ryoto S-970 [3] | 9.95 |
| Mint flavor [4] | 0.5 |
| Water | 79.7 |
| Total | 100 |

[1] Sucrose, Origin: Sigma-Aldrich, Switzerland.
[2] Glyceryl stearate citrate, Origin: Dr Straetmans GmbH, Hamburg, Germany.
[3] Sucrose stearate, Origin: Mitsubishi-Kagaku Foods Corporation, Japan.
[4] Origin and trademark from Firmenich SA, Geneva, Switzerland.

Example 12

Flavored Beads

In a first step, a suspension of liquid crystals in alginate solution was prepared (phase A). To prepare this solution, sucrose was added into water. After homogenization, sodium alginate was added and the solution was mixed until homogeneous. Sugar Ester Ryoto S-970 was added in the alginate solution. The mixture was heated to 75° C. under stirring in water bath. After cooling phase A to room temperature, the flavour (phase B) was added and the mixture was agitated with a stirring motor RW 11 basic "Lab egg" IKA with paddle stirrer R1001 (d=34 mm) at 500/600 rpm for 10 min.

The second step consists in forming spherical beads in a calcium solution (phase C). Alginate solution containing liquid crystals and fragrance was added drop by drop in a water bath containing calcium ions.

After 10 minutes in contact with calcium solution, beads comprising liquid crystalline phases dispersed in the continuous phase (i.e hydrogel matrix) are obtained. Then, they were filtered, washed 3 times and placed in water. The obtained beads show a creamy texture.

TABLE 18

Composition of the different phases involved during the process

| | Ingredient | Function | % wt |
|---|---|---|---|
| Phase A Continuous phase | Water | Aqueous phase | 83.6 |
| | Sucrose [1] | Sugar | 9.5 |
| | Sodium Alginate [2] | Biopolymer | 1.9 |
| | Sugar Ester Ryoto S-970 [3] | Mesogenic compound | 5 |
| Phase B Internal phase | Blueberry flavor [4] | Hydrophobic active ingredient | 100 |
| Phase C | CaCl$_2$ (0.5% wt in water) | Complexing agent | 100 |

TABLE 19

Final composition of flavored alginate beads containing liquid crystals (LC dispersed in the continuous phase)

| Ingredient | % wt |
|---|---|
| Sucrose [1] | 9.49 |
| Sodium Alginate [2] | 1.90 |
| Sugar Ester Ryoto S-970 [3] | 4.99 |
| Blueberry flavor [4] | 0.10 |
| Water | 83.52 |
| Total | 100 |

[1] Sucrose, Origin: Sigma-Aldrich, Switzerland.
[2] Glyceryl stearate citrate, Origin: Dr Straetmans GmbH, Hamburg, Germany.
[3] Sucrose stearate, Origin: Mitsubishi-Kagaku Foods Corporation, Japan.
[4] Flavor, Origin and trademark from Firmenich SA, Geneva, Switzerland.

Example 13

Shampoo Composition Comprising the Hydrogel Beads According to the Invention

1) Shampoo Composition Containing Hydrogel Beads 25 g of hydrogel beads prepared according to example 1 has been added in 100 g of a shampoo base A having the following composition:

TABLE 20

Composition of a shampoo base A

| Product | Description | Concentration [wt %] |
|---|---|---|
| Water | | 33.3 |
| Ucare Polymer JR-400 | Polyquaternium-10 | 0.225 |
| Glycerin 85% | | 0.75 |
| Glydant | DMDM Hydantoin | 0.15 |
| Texapon NSO IS | Sodium Laureth Sulfate | 21 |
| Tego Betain F 50 | Cocamidopropyl Betaine | 2.4 |
| Amphotensid GB 2009 | Disodium Cocoamphodiacetate | 1.5 |
| Texapon NSO IS | Sodium Laureth Sulfate | 3 |
| Monomuls 90 L-12 | Glyceryl Laureate | 0.225 |
| Water deionised | | 0.75 |
| Nipagin Monosodium | Sodium Methylparaben | 0.075 |
| Sodium Chloride 10% aq. | | 11.25 |
| Perfume | | 0.375 |
| Alginate beads of the invention | | 25 |
| Total | | 100 |

2) Shampoo Consumer Product in a Form of Hydrogel Beads

| | Ingredient | % wt |
|---|---|---|
| Phase A Continuous phase | WATER DEIONISED | 75.28 |
| | EDETA B POWDER (Tetrasodium EDETA) | 0.02 |
| | JAGUAR C14 S (Guar Hydroxypropyl-trimonium Chloride) | 0.02 |
| | UCARE POLYMER JR-400 (Polyquaternium-10) | 0.022 |
| | NAOH SOL. 10% | 0.02 |
| | SULFETAL LA B-E (Ammonium Lauryl Sulfate) | 11.13 |
| | ZETESOL LA (Ammonium Laureth Sulfate) | 3.03 |
| | TEGOBETAINE F-50 (Cocamidopropyl Betaine) | 0.65 |
| | XIAMETER MEM-1691 (Dimethicone (&) C12-13 Pareth-4 (&) C12-13 Pareth-23 (and) Salicylic Acid) | 0.82 |
| | CETYL ALCOHOL | 0.4 |
| | COMPERLAN 100 (Cocamide MEA) | 0.50 |
| | CUTINA AGS (Glycol Distearate) | 0.65 |
| | KATHON CG (Methylchloroisothiazolinone & Methylisothiazolinone) | 0.03 |
| | PANTHENOL 75% | 0.03 |
| | WATER DEIONISED | 0.01 |
| | SODIUM CHLORIDE 25% | 0.20 |
| | Sodium Alginate (2% in DI-Water) | 1.89 |
| | Dermofeel GSC | 3.21 |
| | [1]Carbopol ® Aqua SF1 | 2.09 |
| Phase B Internal phase | Fragrance [2] | 100 |
| Phase C | CaCl$_2$ (1% wt water) | 100 |

[1] Acrylates Copolymer; Origin: Lubrizol Corp.
[2] See table 2A

Final Composition of Crystalline Alginate Beads Containing Shampoo Formulation

| Ingredients | % |
|---|---|
| WATER DEIONISED | 74.50 |
| EDETA B POWDER (Tetrasodium EDETA) | 0.02 |
| JAGUAR C14 S (Guar Hydroxypropyltrimonium Chloride) | 0.02 |
| UCARE POLYMER JR-400 (Polyquaternium-10) | 0.02 |
| NAOH SOL. 10% | 0.10 |
| SULFETAL LA B-E (Ammonium Lauryl Sulfate) | 11.19 |
| ZETESOL LA (Ammonium Laureth Sulfate) | 3.04 |
| TEGOBETAINE F-50 (Cocamidopropyl Betaine) | 0.66 |
| XIAMETER MEM-1691 (Dimethicone (&) C12-13 Pareth-4 (&) C12-13 Pareth-23 (and) Salicylic Acid) | 0.82 |
| CETYL ALCOHOL | 0.39 |
| COMPERLAN 100 (Cocamide MEA) | 0.49 |
| CUTINA AGS (Glycol Distearate) | 0.66 |
| KATHON CG (Methylchloroisothiazolinone & Methylisothiazolinone) | 0.03 |
| PANTHENOL 75% | 0.03 |
| WATER DEIONISED | 0.10 |
| SODIUM CHLORIDE 25% | 0.20 |
| Fragrance | 0.50 |
| Sodium Alginate (2% in DI-Water) | 1.90 |
| Dermofeel GSC | 3.23 |
| [1]Carbopol ® Aqua SF1 | 2.10 |
| TOTAL: | 100.00 |

The invention claimed is:

1. A hydrogel bead obtainable by a process comprising the steps of:
   (i) preparing a continuous phase comprising water and a biopolymer;
   (ii) preparing an internal phase comprising an oil phase, and a hydrophobic active ingredient,
   (iii) mixing the continuous phase and the internal phase to form a dispersion,
   (iv) forming a bead by inducing complexation of the dispersion obtained in step (iii), wherein a mesogenic compound is added in step (i) and/or (ii) under conditions that allow the compound to form at least one liquid crystalline structured phase in the hydrogel bead;

wherein step (iv) consists of adding the dispersion of step (iii) in a water bath containing water-soluble complexing agent ions, wherein the biopolymer is chosen from the group consisting of alginates, xanthan, carragenans, chitosan, pectin, gellan, agar-agar, hydroxycellulose, hydroxymethylcellulose, hydroxypropyl cellulose, hydroxyethyl celloluse and mixtures thereof, and wherein the liquid crystalline structured phase is dispersed in the continuous phase or the liquid crystalline structured phase is at the interface between the internal phase and the continuous phase.

2. The hydrogel bead according to claim 1, wherein step (ii) comprises preparing a water-in-oil emulsion or a microcapsule slurry.

3. The hydrogel bead according to claim 1, wherein the weight ratio of complexing agents to biopolymer is between 0.01:1 to 1:0.2.

4. The hydrogel bead according to claim 1, wherein:
the amount of biopolymer is comprised between 0.1 and 10% by weight,
the amount of hydrophobic active is comprised between 0.001 and 50% by weight, and
the amount of mesogenic compound is comprised between 0.0001 and 50% by weight,
based on the total weight of the dispersion.

5. The hydrogel bead according to claim 1, wherein the mesogenic compound is chosen in the group consisting of long chain of alcohols, long chain of fatty acids, long chain of fatty acid salts, long chain of glycerol fatty acids; long chain of lipophilic linear or branched, single or double chained surfactants with HLB<10, long chain of cholesterol esters, polymers and co-polymers having HLB<10, and mixtures thereof.

6. The hydrogel bead according to claim 5, wherein the mesogenic compound is chosen in the group consisting of glyceryl stearate citrate; sucrose stearate; sucrose distearate; myristil alcohol; palmityl alcohol; stearyl alcohol; oleyl alcohol; behenyl alcohol; lauric acid; myristic acid; palmitic acid; stearic acid; oleic acid; linoleic acid; behenic acid; polyglyceryl-10 myristate; lecithins; mixture of steareth-2 and PEG-8 distearate; glyceryl distearate; ethylene glycol distearate; mixture of Cethet-20 and Glyceryl stearate and PEG-6 Stearate and Steareth-20; mixture of Glyceryl Stearate and Polyglyceryl-6 Palmitate and Cetearyl Alcohol; and mixtures thereof.

7. The hydrogel bead according to claim 1, wherein the bead is macroscopic and have a size comprised between 1 mm and 10 mm.

8. The hydrogel bead according to claim 1, wherein the biopolymer is chosen in the group consisting of alginates, xanthan, carragenans, chitosan, pectin, gellan, agar-agar, hydroxycellulose, hydroxymethylcellulose, hydroxypropyl cellulose, hydroxyethyl celloluse and mixtures thereof.

9. The hydrogel bead according to claim 1, wherein the continuous phase and/or the internal phase comprises additional components chosen in the group consisting of surfactants, thickening polymers, pigments, UV filters, aesthetic particles, emollients, hydrating agents, antimicrobial agents, bioactives, cooling agents, preservatives and mixtures thereof.

10. A consumer product comprising a hydrogel bead according to claim 1, wherein the consumer product is in the form of a body care product.

11. A consumer product comprising hydrogel bead according to claim 1, wherein the consumer product is in the form of a flavored product.

* * * * *